(12) United States Patent
Chevillet et al.

(10) Patent No.: US 10,795,440 B1
(45) Date of Patent: Oct. 6, 2020

(54) BRAIN COMPUTER INTERFACE FOR TEXT PREDICTIONS

(71) Applicant: Facebook, Inc., Menlo Park, CA (US)

(72) Inventors: Mark Allan Chevillet, Menlo Park, CA (US); Regina E. Dugan, Los Altos, CA (US); Soo Yeon Kim Jennings, Sunnyvale, CA (US); Michael Andrew Choma, Menlo Park, CA (US); Tobias Gerard Tiecke, Redwood City, CA (US); Patrick Mineault, San Francisco, CA (US); Emily Mittag Mugler, Menlo Park, CA (US); Henry Wettersten, San Francisco, CA (US)

(73) Assignee: Facebook, Inc., Menlo Park, CA (US)

( * ) Notice: Subject to any disclaimer, the term of this patent is extended or adjusted under 35 U.S.C. 154(b) by 137 days.

(21) Appl. No.: 15/955,641

(22) Filed: Apr. 17, 2018

Related U.S. Application Data

(60) Provisional application No. 62/486,257, filed on Apr. 17, 2017.

(51) Int. Cl.
| | |
|---|---|
| *G06F 3/01* | (2006.01) |
| *G06Q 50/00* | (2012.01) |
| *A61B 5/00* | (2006.01) |
| *G10L 15/24* | (2013.01) |
| *A61B 5/0476* | (2006.01) |

(52) U.S. Cl.
CPC ............ *G06F 3/015* (2013.01); *A61B 5/0042* (2013.01); *A61B 5/0476* (2013.01); *G06Q 50/01* (2013.01); *G10L 15/24* (2013.01)

(58) Field of Classification Search
CPC .................................................... G10L 13/027
See application file for complete search history.

(56) References Cited

U.S. PATENT DOCUMENTS 5,357,428 A * 10/1994 Stone, Jr. ............. A61B 5/0478
                                                            600/372
9,646,248 B1 * 5/2017 Benvenuto ............. G06N 5/022
(Continued)

OTHER PUBLICATIONS

Wolpaw, Jonathan R., et al. "Brain-computer interfaces for communication and control." Clinical neurophysiology 113.6 (2002): 767-791. (Year: 2002).*
Amini, Hessam, Hadi Veisi, and Elham Mohammadi. "Target words selection for a persian brain-computer-interface-based speller using language model." 2016 Eighth International Conference on Information and Knowledge Technology (IKT). IEEE, 2016. (Year: 2016).*

(Continued)

*Primary Examiner* — Brian L Albertalli
(74) *Attorney, Agent, or Firm* — Fenwick & West LLP

(57) ABSTRACT

A brain computer interface system interprets an individual's neural signals to predict specific phonemes, words, or sentences, thereby enabling the individual to communicate with others through unspoken methods. Specifically, a brain computer interface system captures neural signals from an individual at mesoscopic resolutions using optical neuroimaging techniques. The system applies the captured neural signals to multiple predictive models that have been trained on neural signals captured from previous individuals. The predictive models output predictions as to a phoneme or word that corresponds to the captured neural signals. Therefore, the individual can communicate through the brain computer interface system by only providing neural signals without using verbal, expressive, or physical means.

18 Claims, 13 Drawing Sheets

(56) References Cited

U.S. PATENT DOCUMENTS

| | | | | |
|---|---|---|---|---|
| 2005/0131311 | A1* | 6/2005 | Leuthardt | A61F 4/00 600/545 |
| 2010/0016752 | A1* | 1/2010 | Sieracki | G10L 13/00 600/544 |
| 2010/0082325 | A1* | 4/2010 | Manuel-Devadoss | G06F 17/28 704/2 |
| 2010/0280403 | A1* | 11/2010 | Erdogmus | A61B 5/0484 600/545 |
| 2011/0046491 | A1* | 2/2011 | Diamond | A61B 5/0073 600/473 |
| 2015/0038812 | A1* | 2/2015 | Ayaz | G06F 3/015 600/328 |
| 2016/0282939 | A1* | 9/2016 | Sorensen | G06F 3/015 |
| 2017/0202476 | A1* | 7/2017 | Desain | A61B 5/7246 |
| 2019/0053734 | A1* | 2/2019 | Schalk | A61N 1/0531 |
| 2019/0380657 | A1* | 12/2019 | Pereira | A61B 34/10 |

OTHER PUBLICATIONS

Herff, Christian, and Tanja Schultz. "Automatic speech recognition from neural signals: a focused review." Frontiers in neuroscience 10 (2016): 429. (Year: 2016).*

Sitaram, Ranganatha, et al. "Temporal classification of multichannel near-infrared spectroscopy signals of motor imagery for developing a brain-computer interface." NeuroImage 34.4 (2007): 1416-1427. (Year: 2007).*

Liljenström, Hans. "Mesoscopic brain dynamics." Scholarpedia 7.9 (2012): 4601. (Year: 2012).*

Speier, William, C. Arnold, and Nader Pouratian. "Integrating language models into classifiers for BCI communication: a review." Journal of neural engineering 13.3 (2016): 031002. (Year: 2016).*

Mora-Cortes, Anderson, et al. "Language model applications to spelling with brain-computer interfaces." Sensors 14.4 (2014): 5967-5993. (Year: 2014).*

* cited by examiner

1100

Receive neural signals obtained with mesoscale resolution from an individual
1105

Pre-process received optical signals
1110

Apply one or more trained predictive models to the pre-processed optical signals
1120

Obtain predicted words as output from the applied trained machine learning model
1130

BRAIN COMPUTER INTERFACE FOR TEXT PREDICTIONS

CROSS REFERENCE TO RELATED APPLICATIONS

This application claims the benefit of U.S. Provisional Application No. 62/486,257, filed on Apr. 17, 2017, which is herein incorporated by reference in its entirety for all purposes.

BACKGROUND

This disclosure generally relates to a brain computer interface (BCI), and more specifically to enabling unspoken communications by translating neuron activity obtained from an individual using a trained predictive model.

Communication via physical actions, such as textual entry or manipulation of a user interface on a mobile or other device is a key form of interaction amongst individuals today. For example, certain online systems, such as online social networks, thrive on the network of users that frequent the online social network on a consistent basis. One component of online social networks is the ability of a user to communicate with others on the online social network by providing comments, content, feedback, and the like to other users of the online social network. In many scenarios, communicating with others on online systems, such as an online social network, requires the user to type or enter words and phrases through a physical means (e.g., a keyboard or clicking on a virtual keyboard). Physically entering words and phrases for communication purposes may be cumbersome or impossible for certain individuals (e.g., quadriplegics, those that have suffered injuries to their extremities, someone on a tightly packed train, or someone whose extremities are occupied). As such, online social networks have difficulty engaging users that may be interested in using the online social network, but are unable to do so due to the difficulty in communicating with others in the online social network. And more generally, physical entry of words and phrases for all individuals is often an inefficient way to communicate as typing or otherwise manipulating various user interfaces can be cumbersome.

Conventional strategies to enable communications in online systems, such as social networks, without the need for physically entering words include voice-to-text options, which can adequately interpret spoken words and phrases and translate them into text. However, voice-to-text options are often inaccurate and face significant privacy concerns. For example, users may prefer not to use conventional strategies such as voice-to-text in public settings where their personal conversations may be readily overheard. As such, conventional strategies for enabling communications in the online social network do not necessarily meet all of the needs of users.

SUMMARY

Disclosed herein are systems and methods for enabling a user to communicate using a brain computer interface (BCI) system through unspoken communications. As used hereafter, unspoken methods and/or unspoken communications refer to communications that can be performed by an individual through non-verbal (e.g., without verbal sounds), non-physical (e.g., not inputted by an individual through a physical means such as a keyboard, mouse, touchscreen, and the like), and non-expressive (e.g., not expressed through facial features, body language, and the like) means.

Generally, a BCI system interprets an individual's neural signals to predict specific phonemes, words, or sentences. Therefore, the individual can communicate with others (e.g., through an online social networking system) using the BCI system through unspoken methods. In particular embodiments, a brain computer interface system captures neural signals (or data that can be later transformed into the neural signals) from an individual at mesoscopic resolutions using optical neuroimaging techniques. The BCI system may include a wearable component, such as a head cap, which is worn by the individual and is further equipped with hardware (e.g., emitters and sensors) that is configured to gather the neural signals from the individual. In one embodiment, the head cap employs optical neuroimaging techniques to gather the neural signals at a mesoscopic spatiotemporal resolution (e.g., ~1 mm spatial resolution, ~100 Hz temporal resolution).

The BCI system applies the captured neural signals to multiple predictive models that have been previously trained on training data. In one embodiment, the predictive models are trained on input data that includes neural signals captured from previous individuals in an experimental setting and on ground truth data that includes a phoneme, word, or sentence that the previous individual was thinking. Therefore, when provided the captured neural signals, the predictive models output a likelihood as to a phoneme or word that corresponds to the captured neural signals. In some embodiments, the BCI system applies a second predictive model that receives the output likelihoods and selects a predicted phoneme or word. In various embodiments, the second predictive model also considers semantic and/or contextual information in selecting a phoneme or word. The BCI system can repeat this process with additional captured neural signals to generate longer words (e.g., from selected phonemes), phrases, and/or sentences for the individual. Therefore, the individual can communicate through the BCI system through non-verbal, non-expressive, and non-physical means by only providing neural signals.

Figure 1:
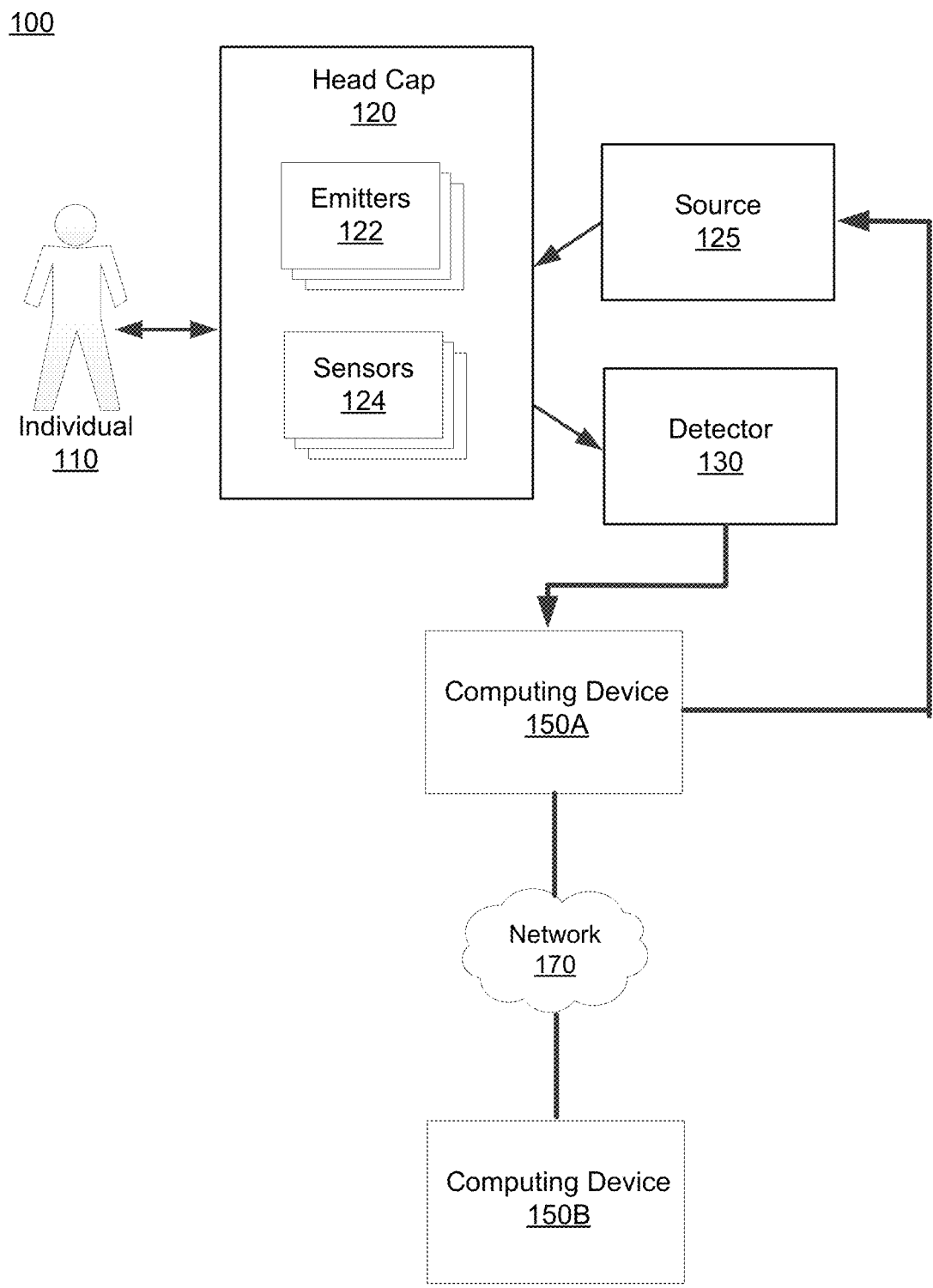
FIG. 1 is an overall system environment for enabling unspoken communications by an individual, in accordance with an embodiment.

The figures depict various embodiments for purposes of illustration only. One skilled in the art will readily recognize from the following discussion that alternative embodiments of the structures and methods illustrated herein may be employed without departing from the principles of the invention described herein.

Reference will now be made in detail to several embodiments, examples of which are illustrated in the accompanying figures. It is noted that wherever practicable similar or like reference numbers may be used in the figures and may indicate similar or like functionality. For example, a letter after a reference numeral, such as "150A," indicates that the text refers specifically to the element having that particular reference numeral. A reference numeral in the text without a following letter, such as "150," refers to any or all of the elements in the figures bearing that reference numeral (e.g. "computing device 150" in the text refers to reference numerals "computing device 150A" and/or "computing device 150B" in the figures).

DETAILED DESCRIPTION

I. Overall System Environment

FIG. 1 depicts an overall system (e.g., a brain computer interface (BCI) system) environment for enabling unspoken communications by an individual 110, in accordance with an embodiment. The overall BCI system 100 may include a head cap 120, a source 125, a detector 130, and one or more computing devices 150 interconnected through a network 170.

The head cap 120 may be worn by an individual 110 and, in some embodiments, can include one or more emitters 122 and one or more sensors 124. The head cap 120 is configured to enable neuroimaging of a location of the individual's brain through a non-invasive method. Specifically, the one or more emitters 122 emits a signal whereas the one or more sensors 124 captures a signal, such as the emitted signal. In some embodiments, the head cap 120 is designed to fully cover the head of the individual 110. In other embodiments, the head cap 120 is designed to cover a portion of the head, depending on which location of the brain the emitters 122 and sensors 124 are intending to gather neural signals from. For example, if the sensors 124 are to gather neural signals corresponding to neurons in the occipital lobe, then the head cap 120 can be designed to reside in contact with the back of the individual's head.

In various embodiments, the emitters 122 and sensors 124 enable the functional neuroimaging in order to gather neural signals from the individual 110 that can be subsequently used to determine the neural activity. For example, the emitters 122 and sensors 124 may be situated close to one another in the head cap 120 in order to target a particular region of the individual's brain. The emitters 122 may emit a signal that is absorbed and/or attenuated by neurons or networks of neurons in the region of the brain. The sensors 124 detect a signal (e.g., backscattered light) from the same region of the brain. In one embodiment, the signal emitted by the emitters 122 and captured by the sensors 124 is infrared light. Therefore, in some embodiments, the detected signal gathered by the sensors 124 can be used to determine a hemodynamic response in the region of the brain.

In some embodiments, the emitters 122 and sensors 124 are embodied in the same structure. For example, the structure may be an optical fiber that can emit a signal and also gather the backscattered signal from the brain. The emitters 122 and sensors 124 are discussed in further detail below.

The source 125 may be in communication with both the computing device 150A and the head cap 120. For example, the source 125 can receives inputs from the computing device 150A and can provide an input to the emitters 122 of the head cap 120. More specifically, the source 125 receives instructions (e.g., turn on, turn off) from the computing device 150A and provides a signal to the emitter 122. In one example, the source 125 may be a laser that provides a signal (e.g., infrared light) through an optical fiber which then emits the signal to the individual's head, as described above. In this example, the emitter 122 is represented by the end of the optical fiber. In another example, the source 125 may be a light emitting diode that provides the signal through an optical fiber such that the emitter 122 can emit a signal.

The detector 130 receives the gathered signals from the sensors 124 of the head cap 120. Although FIG. 1 depicts a single detector 130, there may be multiple detectors 130 in the system that each receives gathered signals from one or more sensors 124 of the head cap 120. As an example, a detector 130 may include a charge coupled device (CCD) that captures signal intensities of signals from one or more sensors 124. As another example, the detector 130 may include a complementary metal oxide semiconductor (CMOS) device that captures signal intensities of signals from one or more sensors 124. In various embodiments, the detector 130 may be coupled to an end of the sensors 124 (e.g., an end of a fiber optic cable) to minimize signal degradation. The detector 130 provides the gathered signals from the sensors 124 to a computing device 150A for further processing.

Examples of a computing device 150 includes a personal computer (PC), a desktop computer, a laptop computer, a notebook, a tablet PC executing an operating system, for example, a Microsoft Windows-compatible operating system (OS), Apple OS X, and/or a Linux distribution. In another embodiment, the computing device 150 can be any device having computer functionality, such as a personal digital assistant (PDA), mobile telephone, smartphone, etc. An example computing device 150 is described below in reference to FIG. 5. The computing device 150 may execute instructions (e.g., computer code) stored on a computer-readable storage medium in order to perform the steps and processes described herein for enabling unspoken communications by an individual 110.

Generally, a computing device 150A predicts phonemes, words, phrases, or sentences given the gathered signals provided by the detector 130. The computing device 150A may determine the neural activity that correspond to the neural signals that were gathered by the detector 130 and applies a predictive model that is trained to predict phonemes, words, phrases, or sentences given the determined neural activity. The computing device 150A may train the predictive model using training data including gathered experimental datasets corresponding to neural activity of previously observed individuals. Altogether, the computing device 150A may predict words, phrases, or sentences for an individual 110 based on the neural signals obtained from the individual.

In some embodiments, a computing device 150A enables a user to access an online social networking system, and therefore, allows users to communicate with one another through the online social networking system. As such, a computing device 150A may communicate on behalf of the individual through the network 170 with other computing devices (e.g., computing device 150B) of the social networking system. In some embodiments, the computing device 150A can communicate on behalf of the individual to other computing devices using the predicted phonemes, words, phrases, and/or sentences.

The network 170 facilitates communications between the one or more computing devices 150. The network 170 may be any wired or wireless local area network (LAN) and/or wide area network (WAN), such as an intranet, an extranet, or the Internet. In various embodiments, the network 170 uses standard communication technologies and/or protocols. Examples of technologies used by the network 170 include Ethernet, 802.11, 3G, 4G, 802.16, or any other suitable communication technology. The network 170 may use wireless, wired, or a combination of wireless and wired communication technologies. Examples of protocols used by the network 170 include transmission control protocol/Internet protocol (TCP/IP), hypertext transport protocol (HTTP), simple mail transfer protocol (SMTP), file transfer protocol (TCP), or any other suitable communication protocol.

II. Neuroimaging Modalities

Different noninvasive optical neuroimaging modalities with different spatiotemporal resolutions can be employed in various embodiments. Noninvasive optical neuroimaging modalities include function near-infrared spectroscopy (fNIRS), functional time-domain near-infrared spectroscopy (TD-fNIRS), diffuse correlation spectroscopy (DCS), speckle contrast optical tomography (SCOT), time-domain interferometric near-infrared spectroscopy (TD-iNIRS), hyperspectral imaging, polarization-sensitive speckle tomography (PSST), spectral decorrelation, auto-fluorescence tomography, and photoacoustic imaging. Non-optical neuroimaging modalities include magnetoencephalography (MEG), electroencephalogram (EEG), positron emission tomography (PET), and functional magnetic resonance imaging (fMRI).

Invasive neuroimaging modalities has the ability to record neural signals with spatiotemporal resolution at the microscopic level. For example, electrocorticography (ECoG) involves the implantation of microelectrodes directly into neural tissue (e.g., cerebral cortex) to record neural signals derived from single neurons. As another example, optical methods such as calcium imaging and voltage sensitive dyes imaging (VSDI) can record signals at a microscopic scale of 1-10 microns over large fields of view. In various embodiments, for a spatial resolution at the single neuron level (e.g., 1-50 μm), neural signals (e.g., synaptic currents of the neuron) can be measured which corresponds to ~1 kHz neural signals. In various embodiments, at the macroscopic scale, neural signals (e.g., EEG readings) that correspond to ~10 Hz neural signals can be obtained from large-scale networks in the brain at a spatial resolution of ~10 millimeters.

Neural signals are recorded noninvasively at the mesoscopic scale via optical methods. In particular, the spatial resolution of a neural signal at the mesoscopic level is between 1 mm and 10 mm and temporal resolution is up to a few seconds (e.g., 0.01 to 1 second). At the mesoscopic scale, ~100 Hz neural signals (e.g., local field potential readings) can be obtained from local networks of neural cells. Mesoscopic resolution is sufficient to enable the implementation of the brain computer interface described herein, and noninvasive technology is beneficial for widespread adoption in a consumer product.

Figure 2:
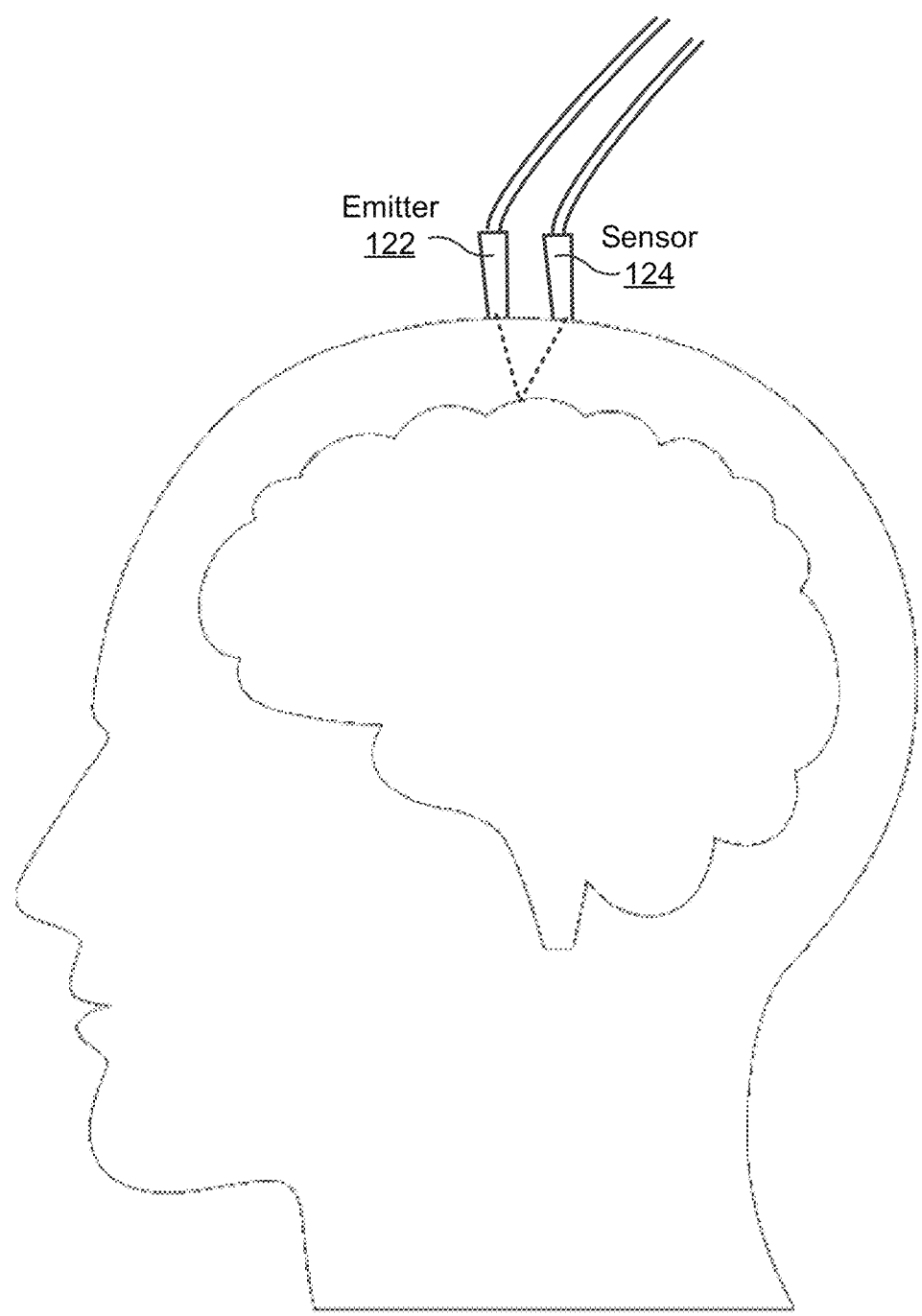
FIG. 2 depicts an example neuroimaging implementation, in accordance with an embodiment.

FIG. 2 depicts an example neuroimaging implementation, in accordance with an embodiment. Specifically, FIG. 2 illustrates an example implementation of optical imaging (e.g., fNIRS) that includes an emitter 122 and a sensor 124. The emitter 122 and the sensor 124 can be components of the wearable head cap 120. In particular embodiments, neural signals are gathered using optical imaging with mesoscopic spatiotemporal resolution as described above. An optical signal with a temporal resolution between 0.01 seconds and 1 second can arise from the interaction of light with neurons. Methods that may be sensitive to light interactions with neurons include methods that capture the scattering of light by neurons and/or coherent interaction of light with neurons. During typical neural activity, neurons may, for example, change in shape, change in refractive index, change in polarization-related properties (e.g. birefringence), change in spectroscopic scattering properties, and change in optical scattering coefficients (e.g. scattering coefficient, reduced scattering coefficient). All of these changes may be evident in the time-varying detected optical signal (e.g. changes in optical speckle turnover rates, changes in optical polarization states). Moreover, these changes are likely to directly reflect changes in neural activity and have a fast response time (temporal resolution between 0.01 seconds and 1 second).

In some embodiments, measurement of neural activity directly (rather than blood oxygenation as is measured in many optical systems) would be accomplished by measuring the intensity of light remitted from the head and additional properties of the optical field. This may include measurements of the time of flight of photons based on time gating using ultrafast detectors or coherence gating, precisely controlling the incident polarization of light and precisely measuring the output polarization, and precise control and measurement of optical phase. In some embodiments, these approaches are implemented using direct detection, and in other cases they are implemented using interferometric detection. In some embodiments, this involves measurement through multimode fibers/waveguides. In other embodiments, measurement will be made through a very large number of single mode fibers/waveguides in order to characterize one or more properties of the optical field in the optical speckle patterns remitted or backscattered from the head.

III. Components of the Overall System

III.A Head Cap

Figure 3A:
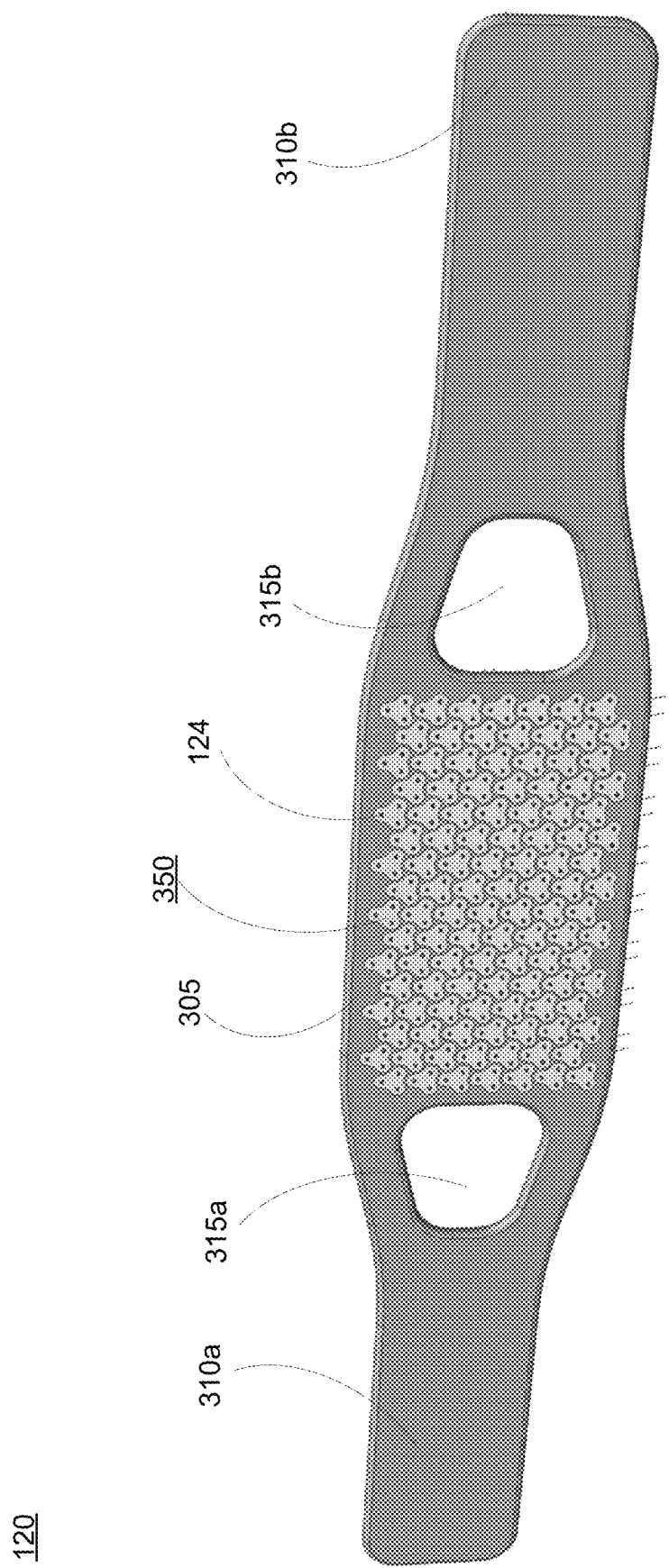
FIG. 3A and FIG. 3B each illustrates an example head cap including multiple sensing units, in accordance with an embodiment.

FIG. 3A illustrates an example head cap 120 including multiple sensing units 350, in accordance with an embodiment. Specifically, FIG. 3A depicts a perspective view of an inner surface 305 of the head cap 120. In various embodiments, the inner surface 305 of the head cap 120 faces the individual's head.

The head cap 120 may include one or more arms 310a and 310b that enable the head cap 120 to be worn on the individual's head. For example, the right arm 310a and the left arm 310b may each be equipped with adhesive patches (e.g., such as VELCRO patches) or fasteners such that when the right arm 310a contacts the left arm 310b, they are adhered to one another. Therefore, the head cap 120 can be worn as a head band around the individual's head, with the right arm 310a and left arm 310b providing the adhesive contact point to form the band. In another example, the adhesive patches of the arms 310 may contact the individual's head, thereby holding the head cap 120 in place while the head cap 120 is worn. One skilled in the art may envision a variety of structures that can enable the head cap 120 to be worn on the individual's head.

The head cap 120 may further include one or more openings 315a and 315b such that the head cap 120 can be worn comfortably by the individual 110. The openings 315a and 315b, as depicted in FIG. 3A, may be configured to relieve excessive pressure on portions of the individual's head when the head cap 120 is worn by the individual. For example, the right opening 315a may align with and receive the individual's right ear whereas the left opening 315b may align with and receive the individual's left ear.

The head cap 120 further includes one or more sensing unit 350. In various embodiments, each sensing unit 350 can be configured to perform a neuroimaging technique and includes both the emitters 122 and sensors 124 of the head cap 120, as described in FIG. 1. For example, each sensing unit 350 can include an emitter 122 to emit a signal and a sensor 124 to detect the emitted signal. In such an example, each sensing unit 350 can perform fNIRS to measure hemodynamic changes in brain tissue, and more specifically, the cerebral cortex. In some embodiments, each sensing unit 350 is an optode, or more specifically, a bio-optode.

Figure 3B:
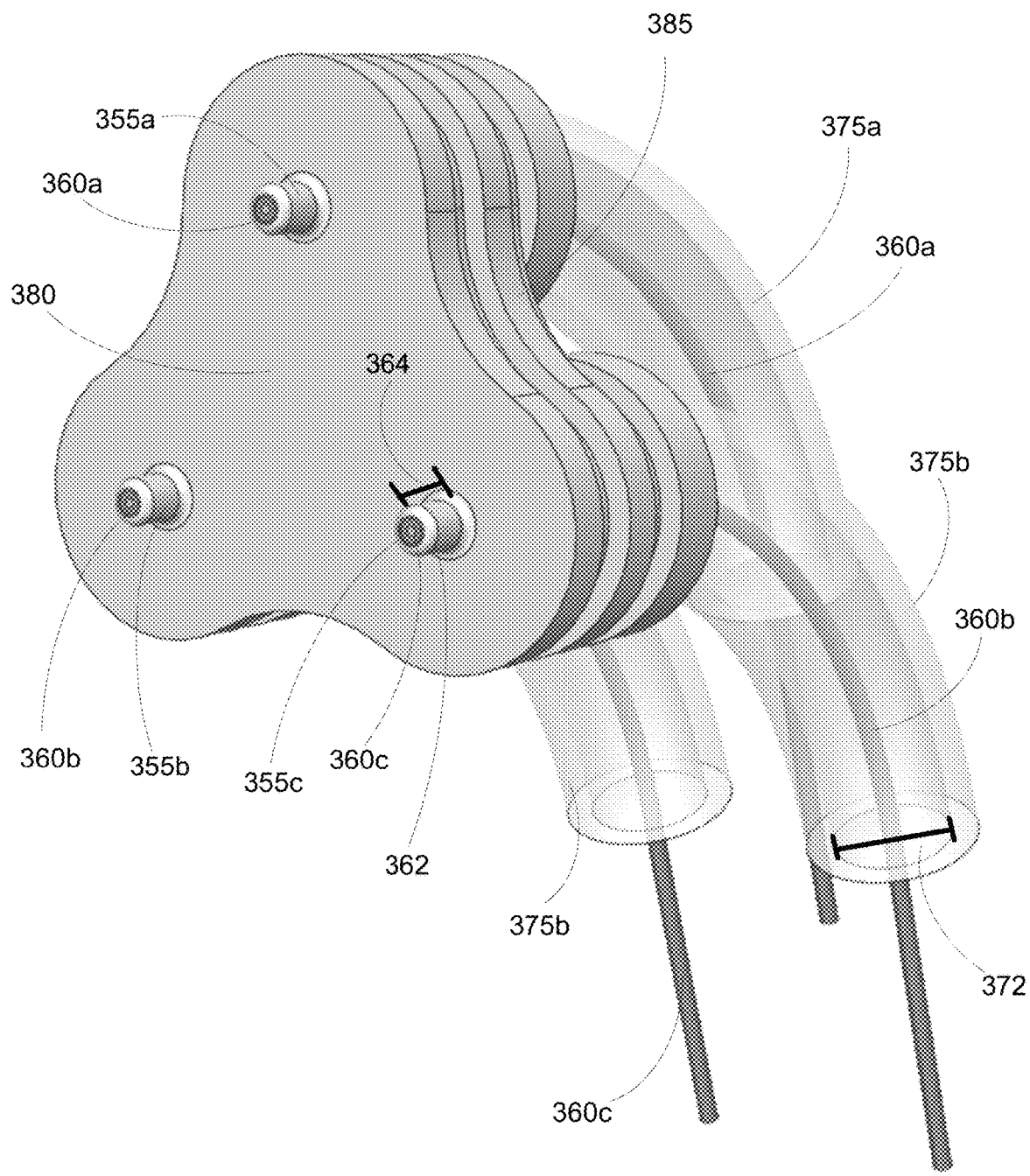

As depicted in FIG. 3A, the sensing units 350 may be designed such that multiple sensing units 350 can be effectively organized into an array on the inner surface 305 of the head cap 120. Reference is now made to FIG. 3B, which depicts an example sensing unit 350, in accordance with an embodiment. As shown in FIG. 3B the sensing unit 350 may be curved such that multiple sensing units 350 can be placed next to one another while maintaining a reduced overall footprint. Specifically, a sensing unit 350 may have one or more recesses 385 such that a portion of another sensing unit 350 may fill in the recess 385 to enable efficient organization of the sensing units 350 as shown in FIG. 3A.

Each individual sensing unit 350 may be a modular structure. Therefore, a modular sensing unit 350 enables the rapid scaling of multiple sensing units 350 that are included in a head cap 120 as depicted in FIG. 3A. In one embodiment, each sensing unit 350 includes three protrusions 355a, 355b, and 355c each extending outward from a face 380 of the sensing unit 350. Each protrusion is cylindrical in shape and may be in contact with an individual's head, thereby enabling neural signals to be gathered by the head cap 120.

In various embodiments, each protrusion 355 is configured to be comfortably in contact with the individual's scalp when the head cap 120 is worn. For example, each protrusion 355 may have a rounded edge 362 (as opposed to a sharp corner or sharp edge) that resides comfortably in contact with the individual's scalp. As another example, each protrusion 355 may have a height 364 that enables the protrusion 355 to adequately penetrate the individual's hair to contact the individual's scalp. The height 364 of each protrusion 355 may be dependent on the quantity/length of the individual's hair. For example, for a bald individual, the height 364 of each protrusion 355 of the sensing unit 350 can be selected to be smaller than the height 364 of each protrusion 355 selected for an individual with a head of hair. In various embodiments, the height 364 of each protrusion 355 is between 0.1 mm and 10 mm, inclusive. In some embodiments, the height 364 of each protrusion 355 is between 0.5 mm and 5 mm. In some embodiments, the height 364 of each protrusion 355 is 1, 2, 3, 4, 5, 6, 7, 8, or 9 mm. In various embodiments, the protrusions 355 are rigid such that the height 364 of each protrusion 355 remains constant even when in contact with an individual's scalp.

Therefore, the protrusion 335 may sit in contact with the individual's scalp while the face 380 of the sensing unit 350 remains a distance (e.g., the height 364) away from the individual's scalp. In some cases, the individual's hair can reside between the face 380 of the sensing unit 350 and the individual's scalp.

In various embodiments, the distance between a first protrusion 355 and a second protrusion 355 is between 1 millimeter and 10 millimeters, inclusive. In particular embodiments, the distance between a first protrusion 355 and a second protrusion 355 is between 3 millimeters and 7 millimeters inclusive. In some embodiments, the distance between two protrusions 355 is 3 mm, 4 mm, 5 mm, 6, mm or 7 mm. The distance between a first protrusion 355 and a second protrusion 355 may be determined based on the desired spatiotemporal resolution of neural signals that are to be gathered.

In various embodiments, each protrusion 355 circumferentially surrounds a fiber 360, such as an optical fiber. In some embodiments, the fiber 360 may serve as both the emitter 122 and the sensor 124 of the head cap 120. As shown in FIG. 3B, each fiber 360 may be exposed on the surface of the protrusion 355 such that when the protrusion 355 sits in contact with the individual's scalp, the fiber 360 can be in contact with the individual's scalp. Therefore, the fiber 360 can emit a signal to a region of the brain and capture the signal from the region of the brain while avoiding the invasive intracranial surgery that is required to access the individual's brain. In particular embodiments, the fiber 360 captures a signal from neurons in the cerebral cortex at a mesoscopic scale. In other embodiments, the fiber captures a signal from neurons in the cerebral cortex at a higher spatial resolution (e.g., single cell resolution).

As further depicted in FIG. 3B, the fibers 360A-C extend from an outer surface of sensing unit 350 through tubes 375A-C. In various embodiments, the tubes 375A-C serve as a protective structure for the fibers 360A-C. For illustrative purposes, FIG. 3B depicts cutaway portions of the tubes 375. In one embodiment, the tubes 375 are strain and stress relieving tubes that minimize the degree of flexion that a fiber 360 experiences when at rest. For example, as depicted in FIG. 3B, a tube 375 may be concentrically located around a fiber 360 and therefore, prevents the fiber 360 from overly deforming or bending which may cause the fiber 360 to break. In one embodiment, each tube 375 may have an inner diameter 372 that matches or is slightly larger than a diameter of the fiber 360. Therefore, as the fiber 360 resides within the tube 375, the curvature/bending of the fiber 360 at rest may be defined by the curvature/bending of a tube 375. The tube 375 may be designed with a material that is less flexible than the fiber 360, thereby ensuring that the stress and strain experienced by the fiber 360 remains minimal. In some embodiments, to prevent excessive stress and strain on the fiber 360, the fiber 360 is adhered to an internal surface of the tube 375.

Figure 3C:
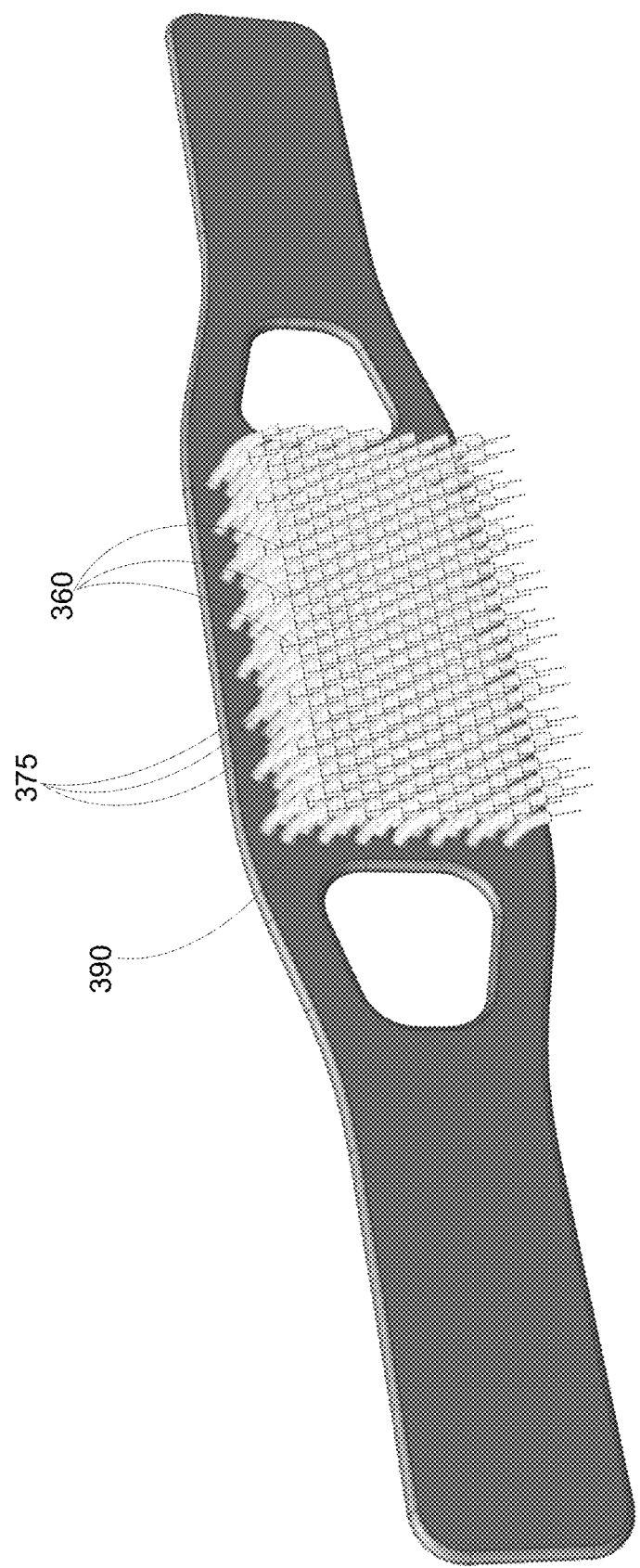
FIG. 3C depicts an example sensing unit of the head cap, in accordance with an embodiment.

FIG. 3C depicts a perspective view of the outer surface 390 of the head cap 120. In one embodiment, the outer surface 390 of the head cap 120 includes multiple tubes 375 that extend away from the outer surface 390, each tube 375 concentrically surrounding a fiber 360. As previously described, the sensing units 350 are designed to be modular and can be organized efficiently for a reduced overall footprint. An added benefit of the efficient organization of the sensing units 350 is the organization of the tubes 375

(and fibers 360) of the multiple sensing units 350 that extend from the outer surface 390 of the head cap 120. The tubes 375 and corresponding fibers 360 are provided to the detector 130.

III.B Detector

Figure 4A:
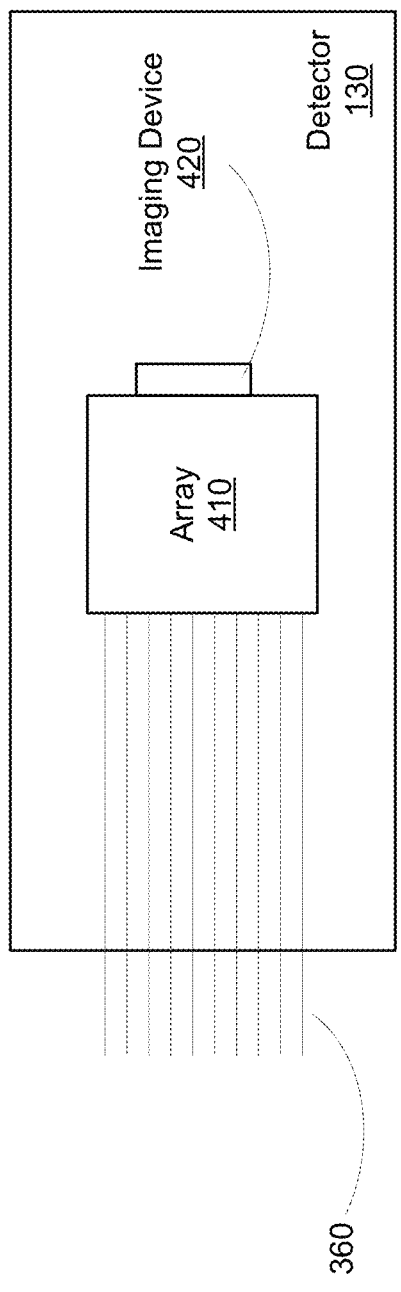
FIG. 4A depicts example components of a detector, in accordance with an embodiment.

FIG. 4A depicts an example detector 130, in accordance with an embodiment. In various embodiments, the detector 130 receives multiple fibers 360 carrying detected signals. The multiple fibers 360 may be further coupled to a specific location on an array 410. Additionally, the detector 130 may include an imaging device 420 that captures images of the array 410. Therefore, the detector 130 can determine multiple neural signals through an image captured by the imaging device 420. In other embodiments, there may be multiple detectors 130 that each receives a single fiber 360 that carries a signal. Therefore, each detector 130 determines a single neural signal. For example, the detector 130 may be an avalanche photodiode (APD) that can determine a neural signal with high sensitivity even if the signal provided by the fiber 360 is weak.

Figure 4B:
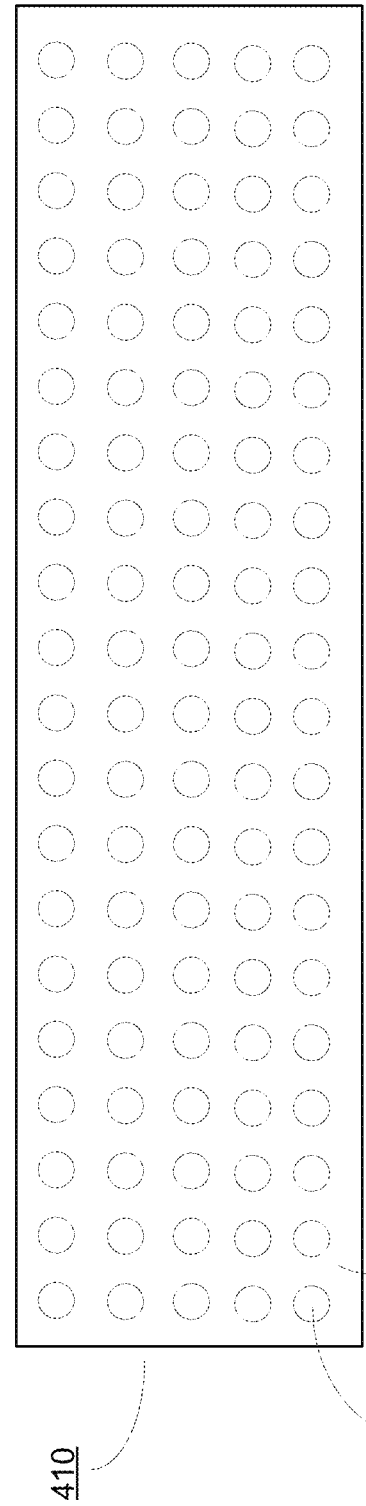
FIG. 4B depicts a frontal view of an array of the detector, in accordance with an embodiment.

In various embodiments, the array 410 is an optical array such as a CMOS array, which is illustrated in FIG. 4B. Specifically, FIG. 4B depicts a frontal view of an array 410 facing the imaging device 420, in accordance with an embodiment. The array 410 may organize the individual fibers 360. For example, as shown in FIG. 4B, the array 410 is a 5×20 array of fibers 360.

In various embodiments, the array 410 may be further designed to ensure that signals from different fibers 360 are not conflated. In other words, the array 410 can be designed to ensure that the signal of each fiber 360 is optically distinct from the signal of another fiber 360. For example, regions 450 within the array 410 between fibers 360 may be generated from an opaque material such that optical signal from one fiber 360 is optically isolated from other optical signals derived from other fibers 360.

The imaging device 420 captures images of the array 410 and determines the intensity of a signal corresponding to each fiber 360. In one embodiment, the imaging device 420 is a CMOS sensor. In another embodiment, the imaging device 420 is a CCD sensor.

In one scenario, each pixel in an image captured by the imaging device 420 corresponds to a location on the array. For example, each pixel may correspond to a fiber 360, and therefore, the imaging device 420 captures an image where each pixel includes signal intensity of each signal from each fiber 360. The detector 130 provides the captured images to the computing device 150 for further analysis.

III.C Computing Device

Figure 5:
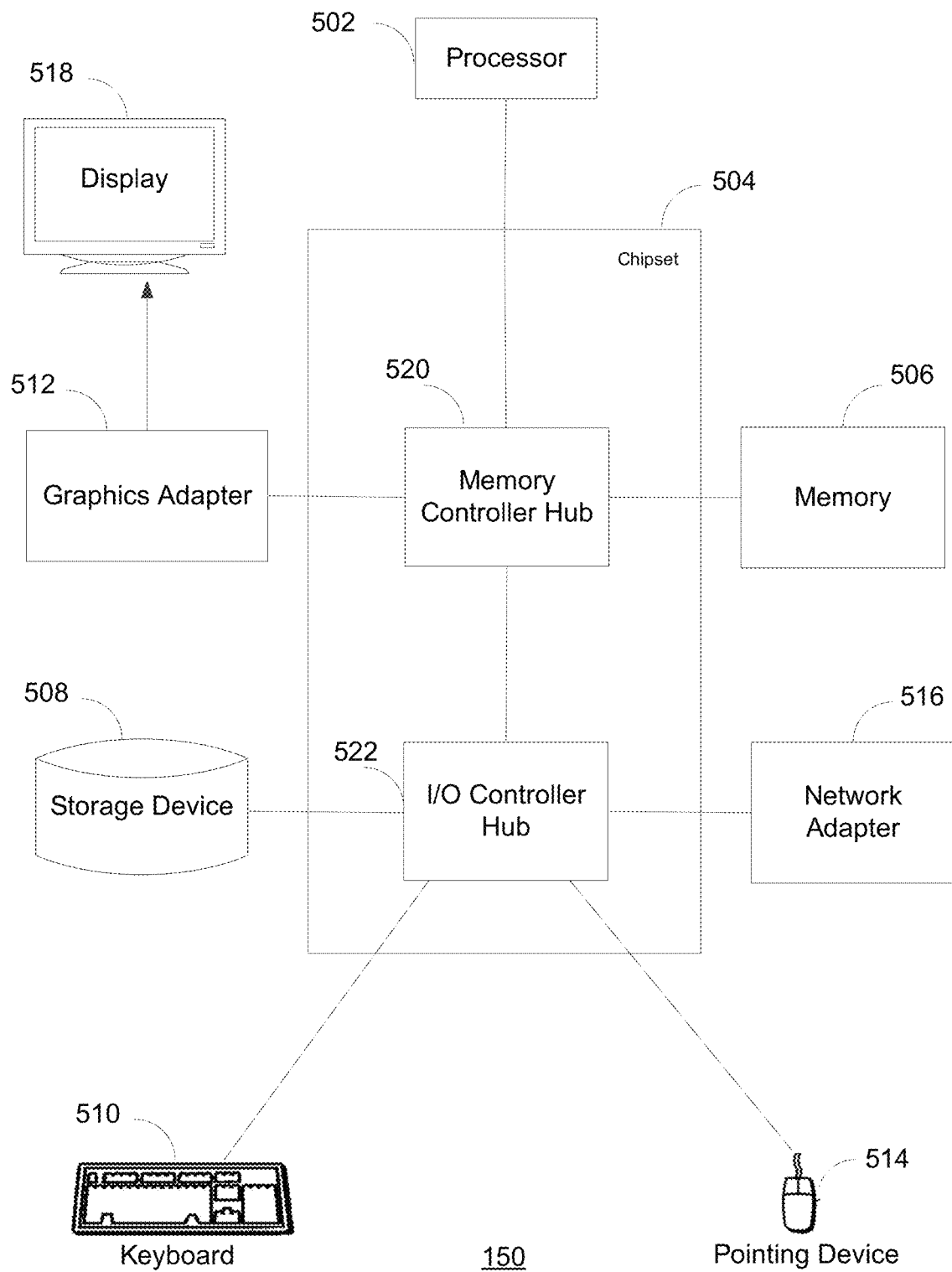
FIG. 5 depicts components of an example computing device, in accordance with an embodiment.

FIG. 5 depicts hardware components of an example computing device 150, in accordance with an embodiment. The computing device 150 may be implemented for the subsequent entities shown in FIG. 6 and FIG. 7. The computing device 150 includes at least one processor 502 coupled to a chipset 504. The chipset 504 includes a memory controller hub 520 and an input/output (I/O) controller hub 522. A memory 506 and a graphics adapter 512 are coupled to the memory controller hub 520, and a display 518 is coupled to the graphics adapter 512. A storage device 508, an input device 514, and network adapter 516 are coupled to the I/O controller hub 522. Other embodiments of the computing device 150 have different architectures.

The storage device 508 is a non-transitory computer-readable storage medium such as a hard drive, compact disk read-only memory (CD-ROM), DVD, or a solid-state memory device. The memory 506 holds instructions and data used by the processor 502. The input interface 514 is a touch-screen interface, a mouse, track ball, or other type of pointing device, a keyboard, or some combination thereof, and is used to input data into the computing device 150. In some embodiments, the computing device 150 may be configured to receive input (e.g., commands) from the input interface 514 via gestures from the user. The graphics adapter 512 displays images and other information on the display 518. As an example, the graphics adapter 512 may display predicted text on the display 518 as feedback to the individual 110. Therefore, the individual 110 may provide feedback to alter the predicted text or can provide an input to send the predicted text to another computing device 150 to communicate the predicted text to another individual. The network adapter 516 couples the computing device 150 to one or more computer networks.

The computing device 150 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 508, loaded into the memory 506, and executed by the processor 502.

The types of computing devices 500 can vary depending upon the embodiment and the processing power required by the entity. For example, the machine learning model module 620 can run in a single computing device 150 or multiple computing devices 150 communicating with each other through a network 170 such as in a server farm. In various embodiments, the computing devices 150 lacks some of the components described above, such as graphics adapters 512, and displays 518.

IV. Methods for Predicting Words from Neural Activity

Figure 6:
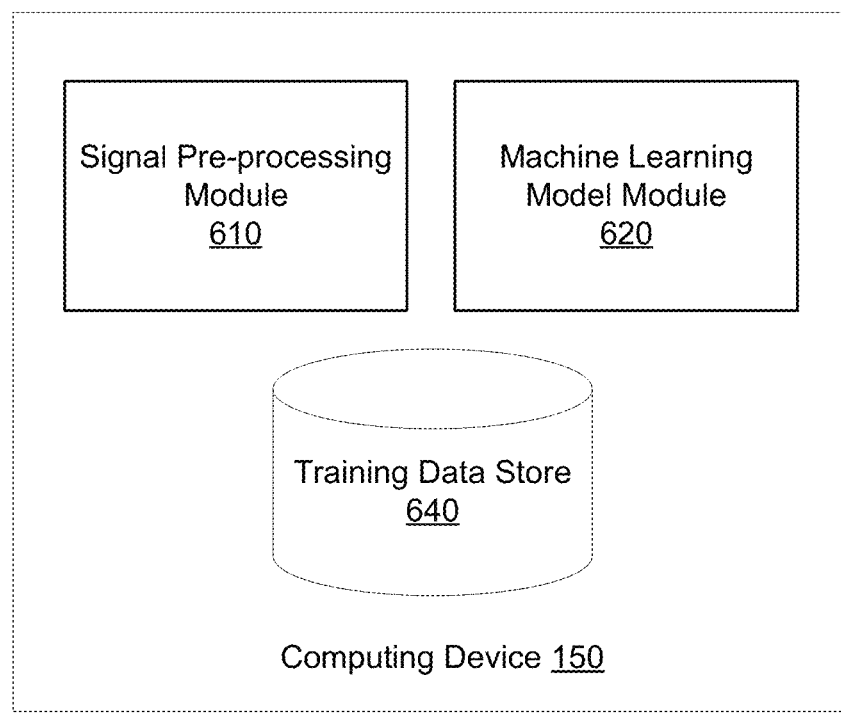
FIG. 6 depicts an example block diagram of the computing device, in accordance with an embodiment.

FIG. 6 depicts an example block diagram of the computing device 150, in accordance with an embodiment. The computing device 150 may include a signal pre-processing module 610, a machine learning model module 620, and a training data store 640.

IV.A Neural Signal Processing

The signal pre-processing module 610 receives the signals captured by the detector 130 and pre-processes the received signal to reconstruct neural signals corresponding to one or more locations in the brain. In one embodiment, the signal pre-processing module 610 applies a filter to remove noise and/or smooth the received signal. In some embodiments, the signal pre-processing module 610 applies a filter to only retain signals in a pre-determined frequency range. As one example, the signal pre-processing module 610 may apply a bandpass filter that allows passage of frequencies that correspond to the high gamma frequency band (70-150 Hz).

In some embodiments, the signal pre-processing module 610 transforms the signal captured by the detector 130 to reconstruct neural signals. For example, if the neuroimaging technique used to gather signals was functional near-infrared spectroscopy (fNIRS), then the signal pre-processing module 610 receives optical signals from the detector 130. The signal pre-processing module 610 determines a hemodynamic response based on the change in optical signals (e.g., a difference between the optical signal gathered by a sensor 124 and the optical signal provided by the emitter 122). Prior studies have shown that neural activity (e.g., neural activity) and hemodynamic response maintain a linear relationship, which is termed "neurovascular coupling." Therefore, the pre-processing module 610 transforms the hemodynamic response (determined based on the gathered signals) to the neural activity.

Figure 8A:
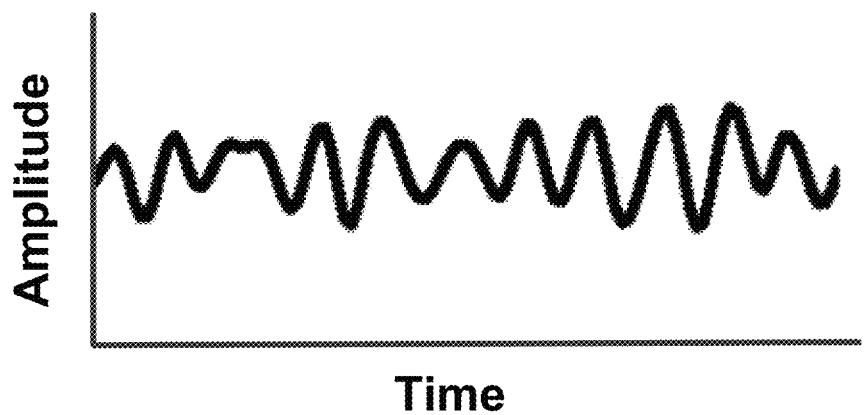
FIG. 8A depicts example neural activity obtained from an individual, in accordance with an embodiment.
Figure 8B:
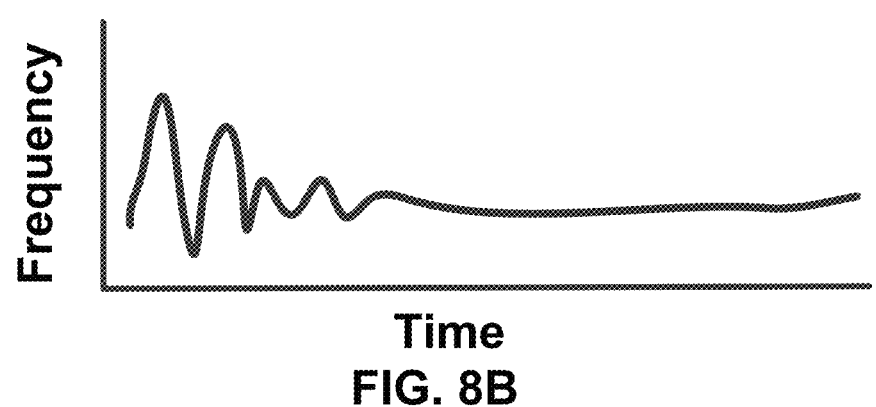
FIG. 8B-8C depict different representations of neural activity, in accordance with an embodiment.
Figure 8C:
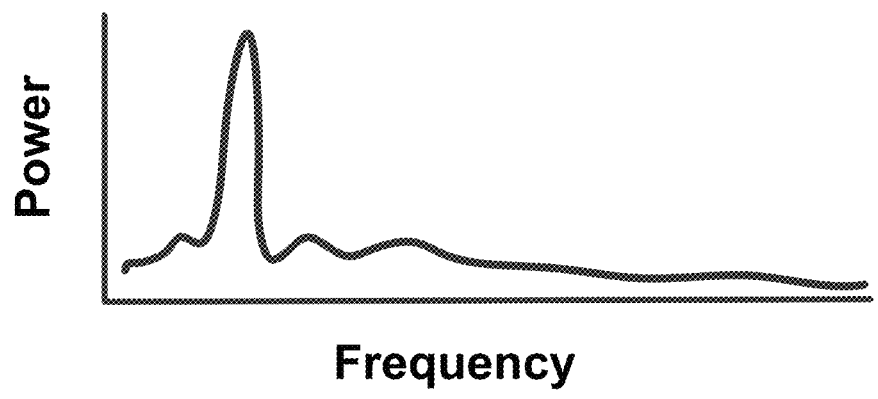

Reference is now made to FIG. 8A, which depicts an example neural activity corresponding to neural signals obtained from an individual, in accordance with an embodiment. In various embodiments, the signal pre-processing module 610 generates neural signals that can be expressed as a plot of signal amplitude as a function of time, as shown in FIG. 8A. The signal pre-processing module 610 may perform additional processing steps to obtain different representations of the neural signal. FIG. 8B and FIG. 8C depict different representations of the neural activity. For example, the signal pre-processing module 610 may generate a spectrogram (see FIG. 8B) which depicts the relationship between frequency as a function of time. Additionally, the signal pre-processing module 610 may generate a power spectral density (see FIG. 8C). In various embodiments, the signal pre-processing module 610 may provide any or all of the different representations of neural signals (e.g., FIG. 8A-8C) to the machine learning model module 620.

Figure 7:
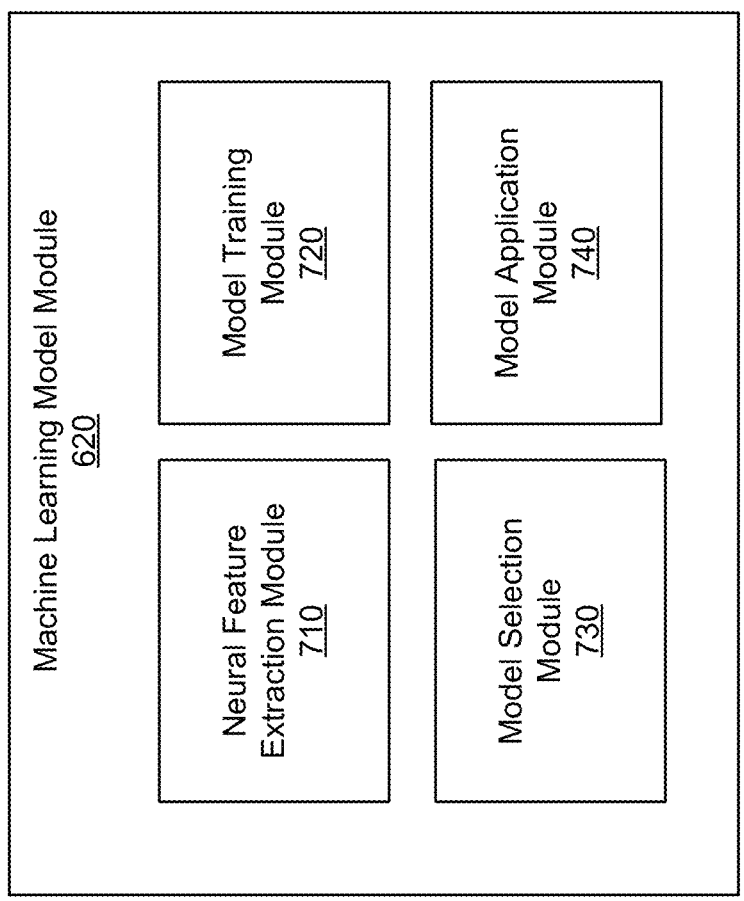
FIG. 7 depicts an example block diagram of the machine learning model module, in accordance with an embodiment.

Reference is now made to FIG. 7, which depicts an example block diagram of the machine learning model module 620, in accordance with an embodiment. In the embodiment shown in FIG. 7, the machine learning model module 620 further includes a neural feature extraction module 710, a model training module 720, a model selection module 730, and a model application module 740. In some embodiments, the machine learning model module 620 may include different modules. For example, in some scenarios, the machine learning model module 620 does not include the neural feature extraction module 710 as the feature extraction process may be learned by a machine learning model as opposed to being conducted by the neural feature extraction module 710.

The neural feature extraction module 710 extracts neural features from the different representations of neural signals provided by the signal pre-processing module 610. Neural features can include one of an amplitude of a neural signal, a maximum amplitude, a period of the neural signal, an aperiodic neural signal, degree of neural firing synchrony, a neural signal duration, a frequency of a neural signal, the absence of a neural signal, a maximum power of a neural signal.

In some embodiments, neural features can also include a change in amplitude or a change in frequency over time. In some embodiments, neural features can be extracted from any of the different neural signal representations by applying a sliding window across the graph. The neural feature extraction module 710 can construct a feature vector that includes the extracted features and provides the feature vector to either the model training module 720 or the model application module 740.

In various embodiments, the model training module 720 trains an overall predictive model, also subsequently referred to as a text prediction model, that receives values of the extracted features and outputs a prediction, such as a predicted phoneme, word, or sentence. In various embodiments, the overall predictive model is one of a decision tree, an ensemble (e.g., bagging, boosting, random forest), linear regression, Naïve Bayes, artificial neural network, or logistic regression. In various embodiments, the overall predictive model is composed of various sub-models, such as individual predictive models. In one embodiment, the model training module 720 may train a first predictive model to predict a likelihood of a phoneme given the neural features. Then the likelihood of the phoneme can be provided as input into a second predictive model to generate a sequence of predicted phonemes, word, or sentence. In these embodiments, the overall predictive model is a two-stage model.

In particular embodiments, the overall predictive model may be trained on training data that includes video and/or audio data. For example, a first sub-model of the overall predictive model may receive values of neural features and output an intermediate representation that represents one or both of video and/or audio features. Therefore, the first sub-model can be trained on the video and/or audio data in the training data to better predict values of video and/or audio features. Such video and/or audio features can serve as input into the second sub-model of the overall predictive model which then outputs a generated phoneme, word, or sentence. Incorporating video and/or audio data can be advantageous to increase the quantity of available training data for training a model that can predict text based on neural features in an efficient manner.

In various embodiments, the overall predictive model may include a first sub-model that models the forward propagation of light from the source through a portion of the individual's brain during a study. Additionally, the overall predictive model may include a second sub-model that models the backward propagation of optical properties from detector to source through an individual's brain at rest, that is when the individual is not thinking in particular or engaged in a particular activity. The first sub-model and second sub-model may predict a neural feature at a common location in the individual's brain, such as a contrast plane located at the cortical surface of the individual's brain. In theory, the first sub-model and second sub-model would align because they each predict an output at a common location; however, in reality, the output predicted by each sub-model may differ, indicative of a change in optical properties from baseline. Here, the difference between the predicted outputs of the first and second sub-models is provided as input to a third sub-model. The third sub-model can generate the predicted output, such as one of a predicted phoneme, word, or sentence. This enables the prediction of text based on neural features derived from the optical signal without having to understand the underlying neurobiology in the individual's brain.

Figure 9:
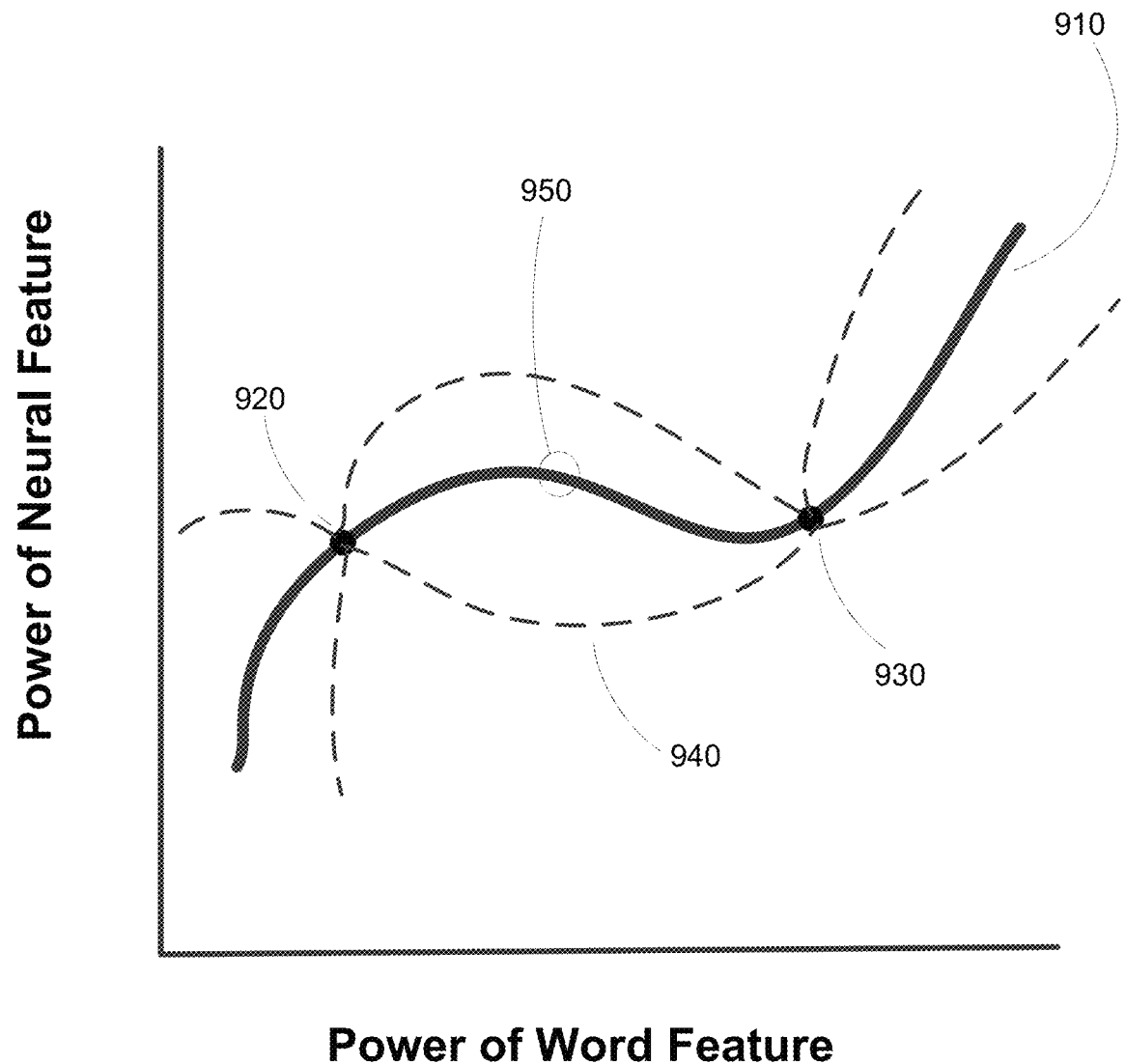
FIG. 9 depicts an example of a predictive model, in accordance with an embodiment.

In various embodiments, the first sub-model of the overall predictive model represents a relationship between neural features (e.g., input) and a feature of a phoneme or word, hereafter referred to as a word feature. Reference is now made to FIG. 9, which depicts an example of a relationship described by the first sub-model, hereafter referred to as a word feature predictive model, in accordance with an embodiment. FIG. 9 depicts a relationship between a power of a neural feature and a power of a word feature. In various embodiments, a word feature is a portion of a word, such as a phoneme or an articulatory gesture (e.g., lip closure). Therefore, for the English language, there may be a total of 44 different word features corresponding to the 44 different phonemes available for the language. Other languages have different numbers of phonemes in their respective languages and therefore, may include a different number of word features.

A word feature predictive model is trained to predict the power of a word feature based on a given power of a neural feature. As an example, FIG. 9 depicts a predicted relationship 910 between the power of a neural feature and a power of a word feature. Therefore, if the predictive model receives, as input, a neural feature extracted from a neural signal obtained from an individual, the word feature predictive model can output a corresponding power of a word feature based on the predicted relationship 910. The output power of a word feature can be used to determine a predicted phoneme.

In various embodiments, the word feature predictive model is a Gaussian Process Regression (GPR) model. In other words, the word feature predictive model includes an uncertainty prediction along with each predicted power of a word feature. As an example, referring back to FIG. 9, assume that two sample points (e.g., sample point 920 and sample point 930) have been sampled from the training data. Therefore, the GPR model has a predictive relationship between the two points. If the GPR model receives a power of a neural feature, the GPR model may output a prediction of the power of the word feature as well as an uncertainty prediction derived from the confidence interval 940. As shown in FIG. 9, the confidence interval of the GPR model widnes as the power of a word feature departs from sample point 920 and sample point 930. In various embodiments, the confidence interval can be a parametric or non-parametric confidence interval.

In some embodiments, a second type of predictive model is also trained to predict a phoneme, word, phrase, or sentence. For example, this predictive model, hereby referred to as a word predictive model, may receive, as input, multiple power of word feature that were outputted by the word feature predictive models described above. Given the various power of word features, the word predictive model may output a predicted phoneme. In some embodiments, the word predictive model may assign different weights to each of the different power of word features from different word feature predictive models in generating the predicted phoneme.

In some embodiments, the word predictive model may consider additional semantic information as input when determining a predicted phoneme. For example, additional semantic information may include a previously predicted phoneme, word, phrase, or sentence. Other examples of semantic information may include a topic or subject matter identified from an ongoing conversation that involves the individual that the predictive model is predicting for. In this embodiment, the word predictive model can output a likely word for the individual using both the multiple power of word features and the semantic information. For example, if the conversation involves the topic of "cookies," the word predictive model can consider this semantic information and assign a higher likelihood to the word "bake" instead of the phonetically similar word "rake."

In various embodiments, the word feature predictive model and the word predictive, as described in the sections above, are embodied in a single predictive model. Thus, this predictive model can receive a feature vector including neural features and outputs a predicted phoneme, word, phrase, or sentence.

IV.B Training Predictive Models

The model training module 720 may train the word feature predictive models and the semantic predictive model using one of a variety of different machine learning techniques including, but not limited to decision tree learning, association rule learning, artificial neural network learning, deep learning, support vector machines (SVM), cluster analysis, Bayesian algorithms, regression algorithms, instance-based algorithms, and regularization algorithms.

In various embodiments, the model training module 720 may iteratively train the word feature predictive models and the word predictive model using training data retrieved from the training data store 640. The training data may include neural signals (e.g., neural signal representations such as FIG. 8A-8C) collected from previous individuals through a conducted experiment. The neural signals in the training data may have corresponding ground truth data that indicates a particular word feature (e.g., phoneme), word, phrase, or sentence that the individual was thinking about when the neural signals were gathered. In some embodiments, predictive models are specifically trained for a particular individual using training data gathered from the individual. Given that there may be variability in neural signals from one individual to another individual, predictive models tailored for specific individuals may avoid the variability.

Each word feature predictive model and word predictive model is iteratively trained on input data that includes the neural signals in the training data. For each iteration, each word feature predictive model receives neural features from the neural signals and generates a predicted power of a word feature. Each word feature predictive model provides its output to the word predictive model which then generates a predicted output, which can be a predicted phoneme, word, phrase, or sentence. The word feature predictive models and the word predictive model are trained to minimize the error between the generated predicted output and the ground truth data.

In various embodiments, the quantity of training data may be limited. Therefore, the model training module 720 may select examples from the training data to train a word feature predictive model. As an example, the model training module 720 may employ active learning in training the multiple word feature models. Referring again to the example word feature predictive model depicted in FIG. 9, the model training module 720 may sample points (e.g., sample point 920 and sample point 930) that define certain points of the relationship between the power of a neural feature and a power of a word feature. Additionally, the word feature predictive model may be a Gaussian Process Regression (GPR) model that includes confidence intervals along the predicted regression. Therefore, the model training module 720 may identify a location along the regression that corresponds to the largest confidence interval and attempts to sample a point that would reduce the confidence interval. As shown in FIG. 9, the model training module 720 may identify sample point 950 as a possible location along the regression that would minimize the confidence interval 940. Therefore, the model training module 720 may identify a training example that has a power of a neural feature that corresponds to sample point 950. In this embodiment where the word feature predictive model is a GPR model, the model training module 720 can train word feature predictive models using fewer examples by identifying optimal sampling points.

In various embodiments, the model training module 720 may store the trained predictive models until they are required at a subsequent time (e.g., during execution).

IV.C Applying Predictive Models

During execution, the computing device 150 receives neural signals from the detector 130 gathered from an individual of interest and predicts phonemes, words, phrases, or sentences by applying the trained predictive models. In some embodiments, the neural feature extraction module 710 extracts neural features from the neural signals to generate a feature vector than can be provided to the appropriate predictive models.

The model selection module 730 identifies the appropriate predictive models (e.g., word feature predictive models and word predictive model) that are to be used during execution. For example, the predictive models that have been previously validated to be the highest performing predictive models are selected during execution.

Figure 10:
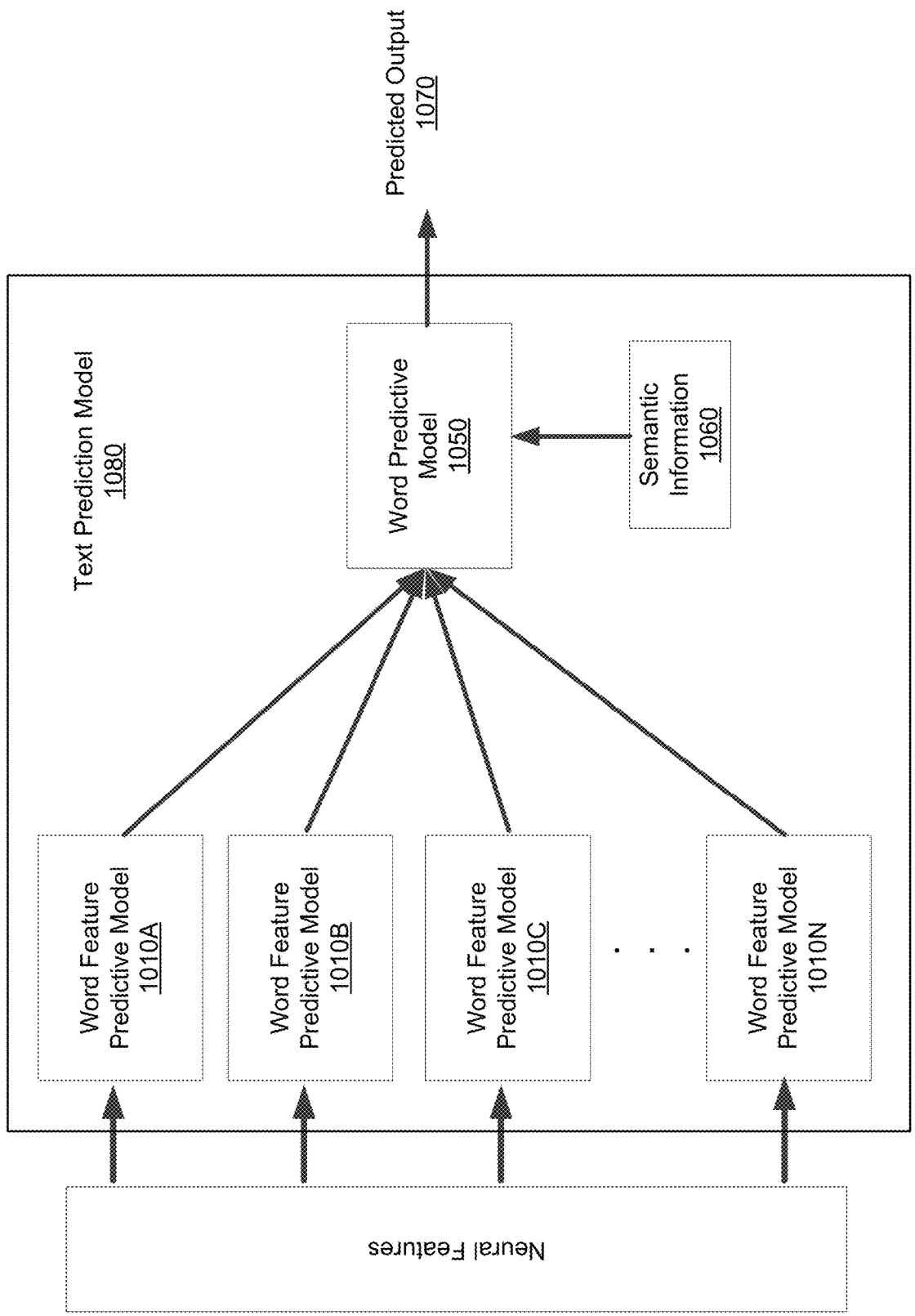
FIG. 10 depicts an example pipeline for predicting a word through the application of multiple predictive models, in accordance with an embodiment.

The model application module 740 applies the predictive models to the received neural signals. Reference is now made to FIG. 10, which depicts an example pipeline for predicting a word through the application of multiple predictive models. Specifically, the neural features can be provided to an overall predictive model, shown in FIG. 10 to be the text prediction model 1080. The text prediction model 1080 can output a predicted output 1070 which can be a predicted phoneme, word, or sentence. The text prediction model 1080 can include one or more first sub-models, shown in FIG. 10 as word feature predictive models 1010. Therefore, in one embodiment, neural features are provided to each predictive model (e.g., word feature predictive model 1010A, word feature predictive model 1010B, word feature predictive model 1010C . . . word feature predictive model 1010N). Each word feature predictive model 1010 generates a power of a word feature that represents the likelihood that the word feature corresponds to an inputted neural feature. The multiple power of word features are provided as input to the word predictive model 1050, which represents the second sub-model of the text prediction model 1080. In various embodiments, the word predictive model 1050 also receives semantic information 1060 as input and generates a predicted output 1070, such as a predicted word. Subsequent new neural features can be provided to the pipeline to generate subsequent words to create phrases and sentences.

V. Example Process of Enabling Unspoken Communications

Figure 11:
FIG. 11 depicts an example flow process for enabling unspoken communications, in accordance with an embodiment.
Figure 11:
Figure 11:

FIG. 11 depicts an example flow process of improving non-verbal communications, in accordance with an embodiment. The BCI system 100 receives 1105 neural signals obtained with mesoscale resolution from an individual. In one embodiment, the neural signals are optical signals captured by an optical detector 130 of the BCI system 100. The captured optical signals may be provided to a computing device 150 that pre-processes 1110 the optical signals. As an example, the computing device 150 may filter out noise and/or signal at unwanted frequencies. In one embodiment, the resulting pre-processed signal corresponds to the high gamma band (70-150 Hz).

The computing device 150 of the BCI system 100 applies 1120 a machine learning model to the pre-processed signal. In various embodiments, the machine learning model is trained to predict a phoneme given an input of a pre-processed signal. In some embodiments, the machine learning model may output multiple predicted phonemes given an input of a pre-processed signal.

The computing device 150 obtains 1130 predicted words as output from the trained predictive model. In various embodiments, the computing device 150 can transmit the predicted words or phrases on behalf of the individual (e.g., as a message) to other computing devices through an online social networking system.

VI. General

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for predicting text by a brain computer interface (BCI) system, the method comprising:
    capturing, by a wearable component of the BCI system that is worn by an individual, neural signals at a mesoscopic scale having a temporal resolution between 0.01 seconds and 1 second and a spatial resolution between 1 mm and 10 mm;
    extracting, by the BCI system, neural features from the captured neural signals; and
    applying at least a word feature predictive model to the extracted neural features to generate a predicted word.

2. The method of claim 1, further comprising:
providing, to a client device, the predicted word on behalf of the individual to enable unspoken communications.

3. The method of claim 1, wherein the wearable component of the BCI system captures neural signals at the mesoscopic scale through an optical fiber circumferentially surrounded by a rigid protrusion of the wearable component, the rigid protrusion having a height such that the protrusion contacts a scalp of the individual.

4. The method of claim 1, wherein the BCI system captures neural signals through an optical neuroimaging technique selected from one of functional near-infrared spectroscopy, functional time-domain near-infrared spectroscopy, diffuse correlation spectroscopy, speckle contrast optical tomography, time-gated interferometric near-infrared spectroscopy, hyperspectral imaging, polarization-sensitive speckle tomography, spectral decorrelation, auto-fluorescence tomography, and photoacoustic imaging.

5. The method of claim 1, wherein capturing neural signals at a mesoscopic scale comprises:
providing, by one or more emitters of the wearable component, an initial optical signal to a region of the brain; and
detecting, by one or more sensors of the wearable component, an optical signal corresponding to the region of the brain.

6. The method of claim 5, wherein capturing neural signals at a mesoscopic scale further comprises:
transmitting, through one or more optical fibers coupled with the wearable component, the optical signal corresponding to the region of the brain.

7. The method of claim 5, wherein capturing neural signals at a mesoscopic scale further comprises:
pre-processing the optical signal to generate neural signals by determining a hemodynamic response based on a difference between the optical signal and the initial optical signal provided to the individual by the one or more emitters of the wearable component of the BCI system.

8. The method of claim 1, wherein the neural features extracted from the captured neural signals are one or more of an amplitude, a maximum amplitude, a period of the neural signal, an aperiodic neural signal, degree of neural firing synchrony, a neural signal duration, a frequency of a neural signal, the absence of a neural signal, a maximum power of a neural signal, a change in amplitude over time of the neural signal, or a change in frequency over time of the neural signal.

9. The method of claim 1, wherein applying at least the word feature predictive model to the extracted neural features to generate a predicted word comprises:
applying a word predictive model, wherein the word feature predictive model describes a relationship between one of the extracted neural features and a word feature, and wherein the word predictive model describes a relationship between the word feature and the predicted word.

10. The method of claim 9, wherein the word predictive model further receives semantic information that provides context for generating the predicted word, the semantic information comprising a previously predicted word.

11. The method of claim 1, wherein the word feature predictive model is a Gaussian process regression (GPR) model, and wherein the word feature predictive model is trained by:
identifying a location along the relationship between one of the extracted neural features and the word feature, the location corresponding to a largest confidence interval; and
training the word predictive model using a training example corresponding to the location along the relationship.

12. A non-transitory computer readable medium comprising instructions that, when executed by a processor of a brain computer interface (BCI) system, cause the processor to:
capture, by a wearable component of the BCI system that is worn by an individual, neural signals at a mesoscopic scale having a temporal resolution between 0.01 seconds and 1 second and a spatial resolution between 1 mm and 10 mm;
extract, by the BCI system, neural features from the captured neural signals; and
apply at least a word feature predictive model to the extracted neural features to generate a predicted word.

13. The non-transitory computer readable medium of claim 12, wherein the BCI system captures neural signals through an optical neuroimaging technique selected from one of functional near-infrared spectroscopy, functional time-domain near-infrared spectroscopy, diffuse correlation spectroscopy, speckle contrast optical tomography, time-gated interferometric near-infrared spectroscopy, hyperspectral imaging, polarization-sensitive speckle tomography, spectral decorrelation, auto-fluorescence tomography, and photoacoustic imaging.

14. The non-transitory computer readable medium of claim 12, wherein the instructions that cause the processor to capture neural signals at a mesoscopic scale further comprise instructions that, when executed by the processor, cause the processor to:
provide, by one or more emitters of the wearable component, an initial optical signal to a region of the brain; and
detect, by one or more sensors of the wearable component, an optical signal corresponding to the region of the brain.

15. The non-transitory computer readable medium of claim 12, wherein the instructions that cause the processor to capture neural signals at a mesoscopic scale comprises instructions that, when executed by the processor, cause the processor to:
transmit, through one or more optical fibers coupled with the wearable component, the optical signal corresponding to the region of the brain.

16. The non-transitory computer readable medium of claim 14, wherein the instructions that cause the processor to capture neural signals at a mesoscopic scale further comprises instructions that, when executed by the processor, cause the processor to:
pre-process the optical signal to generate neural signals by determining a hemodynamic response based on a difference between the optical signal and the initial optical signal provided to the individual by the one or more emitters of the wearable component of the BCI system.

17. The non-transitory computer readable medium of claim 12, wherein the instructions that cause the processor to apply at least the word feature predictive model to the extracted neural features to generate a predicted word further comprises instructions that, when executed by the processor, cause the processor to:
apply a word predictive model, wherein the word feature predictive model describes a relationship between one of the extracted neural features and a word feature, and wherein the word predictive model describes a relationship between the word feature and the predicted word.

18. A brain computer interface system comprising:
a head cap wearable by an individual for optical neuroimaging of the individual's brain, the head cap comprising at least one emitter and at least one sensor for capturing neural signals from the individual at a mesoscopic scale having a temporal resolution between 0.01 seconds and 1 second and a spatial resolution between 1 mm and 10 mm;
a computing device configured to receive the neural signals at the mesoscopic scale from the head cap, the computing device comprising:
 a neural feature extraction module to extract neural features from the captured neural signals; and
 a model application module coupled to the neural feature extraction module to apply the extracted neural features to a text prediction model to obtain predicted text; and
an output display coupled to the computing device and configured to display the predicted text.

* * * * *